United States Patent
Ou Yang et al.

(10) Patent No.: US 11,160,462 B2
(45) Date of Patent: Nov. 2, 2021

(54) PHYSIOLOGICAL STATUS MONITORING DEVICE

(71) Applicant: AVITA CORPORATION, New Taipei (TW)

(72) Inventors: Hsing Ou Yang, New Taipei (TW); Hsuan Hao Shih, New Taipei (TW); Ta Chieh Yang, New Taipei (TW)

(73) Assignee: AVITA CORPORATION, New Taipei (TW)

(*) Notice: Subject to any disclaimer, the term of this patent is extended or adjusted under 35 U.S.C. 154(b) by 598 days.

(21) Appl. No.: 15/402,224

(22) Filed: Jan. 9, 2017

(65) Prior Publication Data
US 2017/0196466 A1 Jul. 13, 2017

(30) Foreign Application Priority Data
Jan. 8, 2016 (TW) .................. 105100615

(51) Int. Cl.
*A61B 5/0205* (2006.01)
*A61B 5/00* (2006.01)
*A61B 5/08* (2006.01)
*A61B 5/01* (2006.01)
(Continued)

(52) U.S. Cl.
CPC .......... *A61B 5/02055* (2013.01); *A61B 5/002* (2013.01); *A61B 5/0002* (2013.01);
(Continued)

(58) Field of Classification Search
CPC ..... A61B 5/02055; A61B 5/6804; A61B 5/08; A61B 5/02438; A61B 5/01; A61B 5/0002; A61B 5/002; A61B 4/0017; A61B 5/0008; A61B 5/7475; A61B 5/746; A61B 5/0816; A61B 5/024; A61B 2560/0443;
(Continued)

(56) References Cited

U.S. PATENT DOCUMENTS

| 9,057,647 B2 | 6/2015 | Chen et al. |
| 2007/0299325 A1 | 12/2007 | Farrell et al. |

(Continued)

FOREIGN PATENT DOCUMENTS

| CN | 1502976 A | 6/2004 |
| CN | 201740598 U | 2/2011 |

(Continued)

*Primary Examiner* — Gary Jackson
*Assistant Examiner* — Sebastian X Lukjan
(74) *Attorney, Agent, or Firm* — Raymond Chan

(57) ABSTRACT

A physiological status monitoring device includes a monitoring module and a fixing module. The monitoring module includes a first housing configured to be arranged at a first side of a flexible object, a monitoring unit arranged in the first housing for monitoring a physiological status of a human body, a first processing unit electrically connected to the monitoring unit for controlling operations of the monitoring unit, and a first magnetic fixing unit connected to the first housing. The fixing module includes a second housing configured to be arranged at a second side of the flexible object, and a second magnetic fixing unit connected to the second housing. Wherein, the first magnetic fixing unit and the second magnetic fixing unit are configured to hold the first housing and the second housing on the flexible object by magnetic force.

10 Claims, 2 Drawing Sheets

(51) Int. Cl.
*A61B 5/024* (2006.01)
*H04W 4/80* (2018.01)

(52) U.S. Cl.
CPC ............ *A61B 5/01* (2013.01); *A61B 5/02438* (2013.01); *A61B 5/08* (2013.01); *A61B 5/6804* (2013.01); *H04W 4/80* (2018.02); *A61B 5/0008* (2013.01); *A61B 5/0017* (2013.01); *A61B 5/0024* (2013.01); *A61B 5/024* (2013.01); *A61B 5/0816* (2013.01); *A61B 5/742* (2013.01); *A61B 5/746* (2013.01); *A61B 5/7475* (2013.01); *A61B 2560/045* (2013.01); *A61B 2560/0406* (2013.01); *A61B 2560/0443* (2013.01)

(58) Field of Classification Search
CPC .................. A61B 5/742; A61B 5/0024; A61B 2560/0406; A61B 2560/045; A61B 5/683; A61B 5/6887; H04W 4/80
See application file for complete search history.

(56) References Cited

U.S. PATENT DOCUMENTS

| | | |
|---|---|---|
| 2008/0319325 A1 | 12/2008 | Tatara et al. |
| 2010/0308187 A1 | 12/2010 | Lin |
| 2012/0296174 A1* | 11/2012 | McCombie ........ A61B 5/02427 600/301 |
| 2013/0338472 A1* | 12/2013 | Macia Barber .... A61B 5/04085 600/388 |
| 2014/0316229 A1* | 10/2014 | Tognetti ............... A61B 5/6802 600/383 |
| 2015/0238118 A1 | 8/2015 | Legassey et al. |
| 2015/0241931 A1* | 8/2015 | Carnevali ............... G06F 1/181 361/679.41 |

FOREIGN PATENT DOCUMENTS

| | | | |
|---|---|---|---|
| CN | 201985859 | 9/2011 | |
| DE | 202008017766 U1 | 6/2010 | |
| JP | H08308805 | 11/1996 | |
| JP | 2001017396 | 1/2001 | |
| JP | 2001099463 | 4/2001 | |
| JP | 2003019008 | 1/2003 | |
| JP | 2004515291 | 5/2004 | |
| JP | 2010148729 | 7/2010 | |
| JP | 2011138530 | 7/2011 | |
| TW | 200512441 | 4/2005 | |
| TW | M331365 | 5/2008 | |
| TW | 1347179 | 8/2011 | |
| TW | M463572 | 10/2013 | |
| WO | WO-2015059700 A1 * | 4/2015 | ............ A61B 5/087 |
| WO | WO2015/137794 | 9/2015 | |

* cited by examiner

PHYSIOLOGICAL STATUS MONITORING DEVICE

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

The present invention relates to a physiological status monitoring device, and more particularly, to a physiological status monitoring device capable of being easily fixed on a flexible object.

2. Description of Related Arts

In order to monitor body temperature, heart rate, respiration or other physiological status of a human body (such as a patient, an old person, or an infant) for a long time, a physiological status monitoring device of the prior art is required to be attached to skin so as to continuously or periodically monitor the physiological status of the human body. However, when the physiological status monitoring device is attached to the skin for a long time, an adhesive material of the physiological status monitoring device may cause skin allergy or discomfort for a user. The physiological status monitoring device of the prior art is not comfortable to wear, so as to reduce wearing willingness of the user. As such, the physiological status monitoring device of the prior art cannot effectively and properly perform functions.

SUMMARY OF THE PRESENT INVENTION

The present invention provides a physiological status monitoring device comprising a monitoring module and a fixing module. The monitoring module comprises a first housing configured to be arranged at a first side of a flexible object, a monitoring unit arranged in the first housing for monitoring a physiological status of a human body, a first processing unit electrically connected to the monitoring unit for controlling operations of the monitoring unit, and a first magnetic fixing unit connected to the first housing. The fixing module comprises a second housing configured to be arranged at a second side of the flexible object, and a second magnetic fixing unit connected to the second housing. Wherein, the first magnetic fixing unit and the second magnetic fixing unit are configured to hold the first housing and the second housing on the flexible object by magnetic force.

In an embodiment of the present invention, the monitoring unit is a non-contact type monitoring unit.

In an embodiment of the present invention, the monitoring unit is configured to monitor body temperature, heart rate and/or respiration of the human body.

In an embodiment of the present invention, one of the first housing and the second housing has a recessed structure, and the other one of the first housing and the second housing has a protrusion structure corresponding to the recessed structure. The protrusion structure and the recessed structure are configured to be engaged with each other for holding the flexible object.

In an embodiment of the present invention, the physiological status monitoring device further comprises an indication light for indicating a monitoring result of the monitoring unit In an embodiment of the present invention, the monitoring module further comprises a wireless transmission module for wirelessly transmitting the monitoring result of the monitoring unit.

In an embodiment of the present invention, the wireless transmission module is a Bluetooth transmission module for wirelessly transmitting the monitoring result to an external electronic device.

In an embodiment of the present invention, the fixing module further comprises a wireless receiver module configured to receive the monitoring result transmitted from the wireless transmission module, a display unit, and a second processing unit electrically connected to the wireless receiver module and the display unit for controlling the display unit to display the monitoring result.

In an embodiment of the present invention, the wireless transmission module is an infrared transmission module and the wireless receiver module is an infrared receiver module.

In an embodiment of the present invention, the physiological status monitoring device further comprises a switch configured to generate a control signal to the first processing unit.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENT

Figure 1:
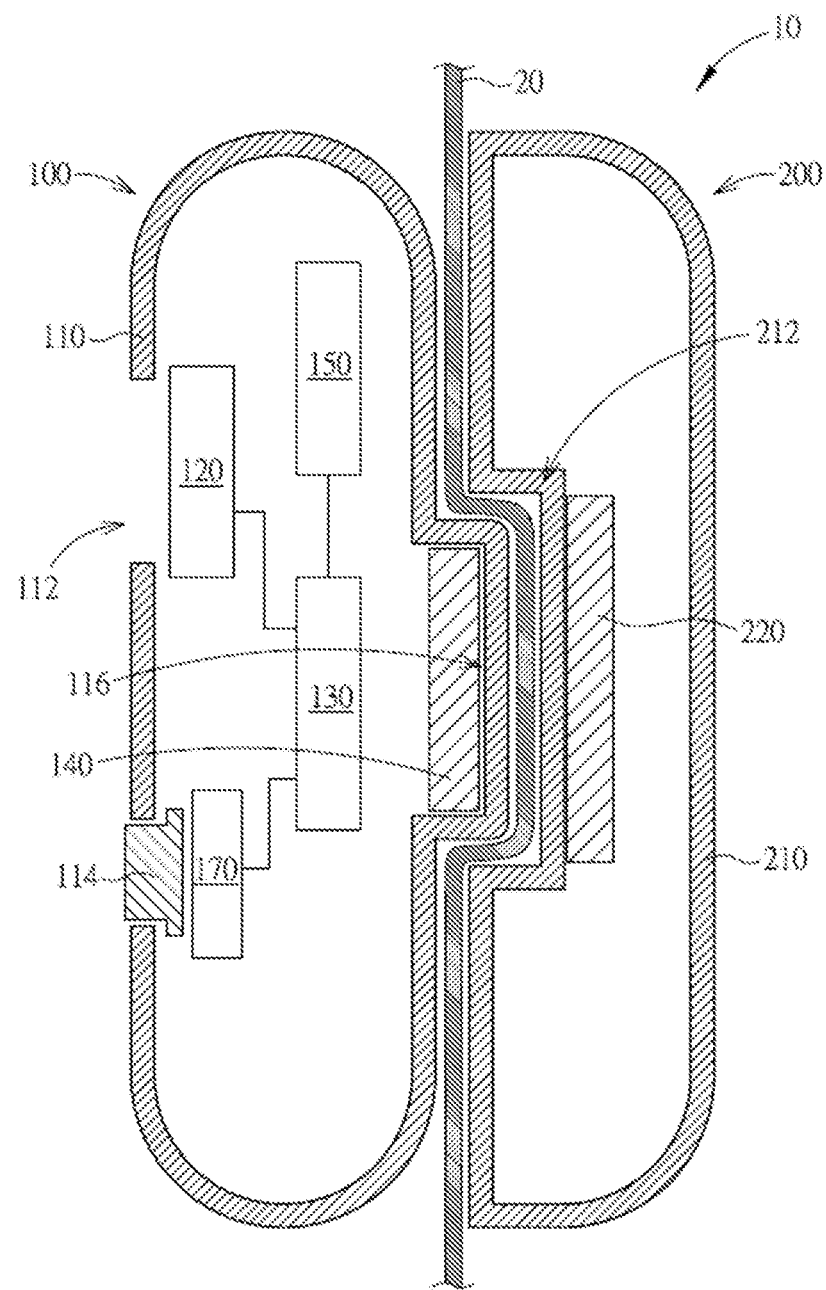
FIG. 1 is a diagram showing a first embodiment of a physiological status monitoring device of the present invention.

Please refer to FIG. 1. FIG. 1 is a diagram showing a first embodiment of a physiological status monitoring device of the present invention. As shown in FIG. 1, the physiological status monitoring device 10 of the present invention comprises a monitoring module 100 and a fixing module 200. The monitoring module 100 comprises a first housing 110, a monitoring unit 120, a first processing unit 130 and a first magnetic fixing unit 140. The fixing module 200 comprises a second housing 210 and a second magnetic fixing unit 220. The first housing 110 is configured to be arranged at a first side of a flexible object 20 (such as an inner side of clothes or a blanket). An accommodating space is formed in the first housing 110. The monitoring unit 120 is arranged in the first housing 110 for monitoring a physiological status of a human body. For example, the monitoring unit 120 can be a contact type or non-contact type monitoring unit for monitoring body temperature, heart rate and/or respiration of the human body. In addition, an opening can be formed on the first housing 110 for allowing the monitoring unit 120 to face the human body for monitoring. The first processing unit 130 is electrically connected to the monitoring unit 120 for controlling operations of the monitoring unit 120. For example, the processing unit 130 can continuously or periodically control the monitoring unit 120 to monitor the physiological status of the human body according to a setting of a user. The first magnetic fixing unit 140 is connected to the first housing 110.

The second housing 210 of the fixing module 200 is configured to be arranged at a second side (of the flexible object 20 such as an outer side of the clothes or blanket). The second magnetic fixing unit 220 is connected to the second housing 210. The first magnetic fixing unit 140 and the second magnetic fixing unit 220 are configured to hold the first housing 110 and the second housing 210 on the flexible object 20 by magnetic force. For example, the first magnetic fixing unit 140 can be made of a magnetic material (such as iron, cobalt, nickel), and the second magnetic fixing unit 220 can be a permanent magnet for attracting the first magnetic fixing unit 140. As such, the first housing 110 and the second housing 210 can be held on the flexible object 20 by a magnetic force between the first magnetic fixing unit 140 and the second magnetic fixing unit 220. But the present invention is not limited thereto. In other embodiments of the present invention, both the first magnetic fixing unit 140 and the second magnetic fixing unit 220 can be permanent magnets, and the first magnetic fixing unit 140 and the second magnetic fixing unit 220 are configured to attract each other; or the first magnetic fixing unit 140 can be a permanent magnet, ad the second magnetic fixing unit 220 can be made of a magnetic material.

On the other hand, in order to prevent the first housing 110 and the second housing 120 from slipping on the flexible object 20, the first housing 110 can have a protrusion structure 116 and the second housing 210 can have a recessed structure 212. The protrusion structure 116 corresponds to the recessed structure 212, and the protrusion structure 116 and the recessed structure 212 are configured to be engaged with each other for clamping the flexible object 20, such that the first housing 110 and the second housing 120 can be prevented from slipping on the flexible object 20. But the present invention is not limited thereto. In other embodiments of the present invention, positions of the protrusion structure and the recessed structure can be switched. That is, the first housing 110 has the recessed structure and the second housing 210 has the protrusion structure. Or, each of the first housing 110 and the second housing 210 can have both the protrusion structure and recessed structure.

According to the above arrangement, the physiological status monitoring device 10 of the present invention can be fixed to the flexible object by the magnetic force in order to monitor the physiological status of the human body for a long time without being attached to skin. Therefore, the physiological status monitoring device 10 of the present invention can prevent skin allergy or discomfort caused by attaching the physiological status monitoring device 10 to the skin.

Moreover, the monitoring device 100 can further comprise a first wireless transmission module 150 for wirelessly transmitting a monitoring result of the monitoring unit 120. For example, the wireless transmission module can be a Bluetooth transmission module for wirelessly transmitting the monitoring result to an external electronic device, such as a smart phone or a computer, so as to allow medical personnel or related personnel to watch the monitoring result at any time.

On the other hand, the monitoring module 100 can further comprise a switch 170 for generating a control signal to the first processing unit 130. For example, the switch 170 can be a pushbutton switch. The first housing 110 can further has a pressing structure 114 corresponding to the switch 170. When the pressing structure 114 is pressed, the switch 170 is activated to generate a control signal to the first processing unit 130. The first processing unit 130 can control the monitoring unit 120 to perform a corresponding operation (such as measuring the physiological status of the human body) according to the control signal. As such, in addition to continuously or periodically monitoring the physiological status of the human body according to the setting of the user, the monitoring unit 120 can also monitor the physiological status of the human body at any time based on using requirements by activating the switch 170. Moreover, in the present invention, the switch 170 is not limited to the pushbutton switch. The switch 170 can be selected from other types of switches, such as a touch sensing switch. The user can activate the switch by touch. When the switch 170 is a touch sensing switch or other type of switch, the first housing 110 can have another corresponding structure.

Figure 2:
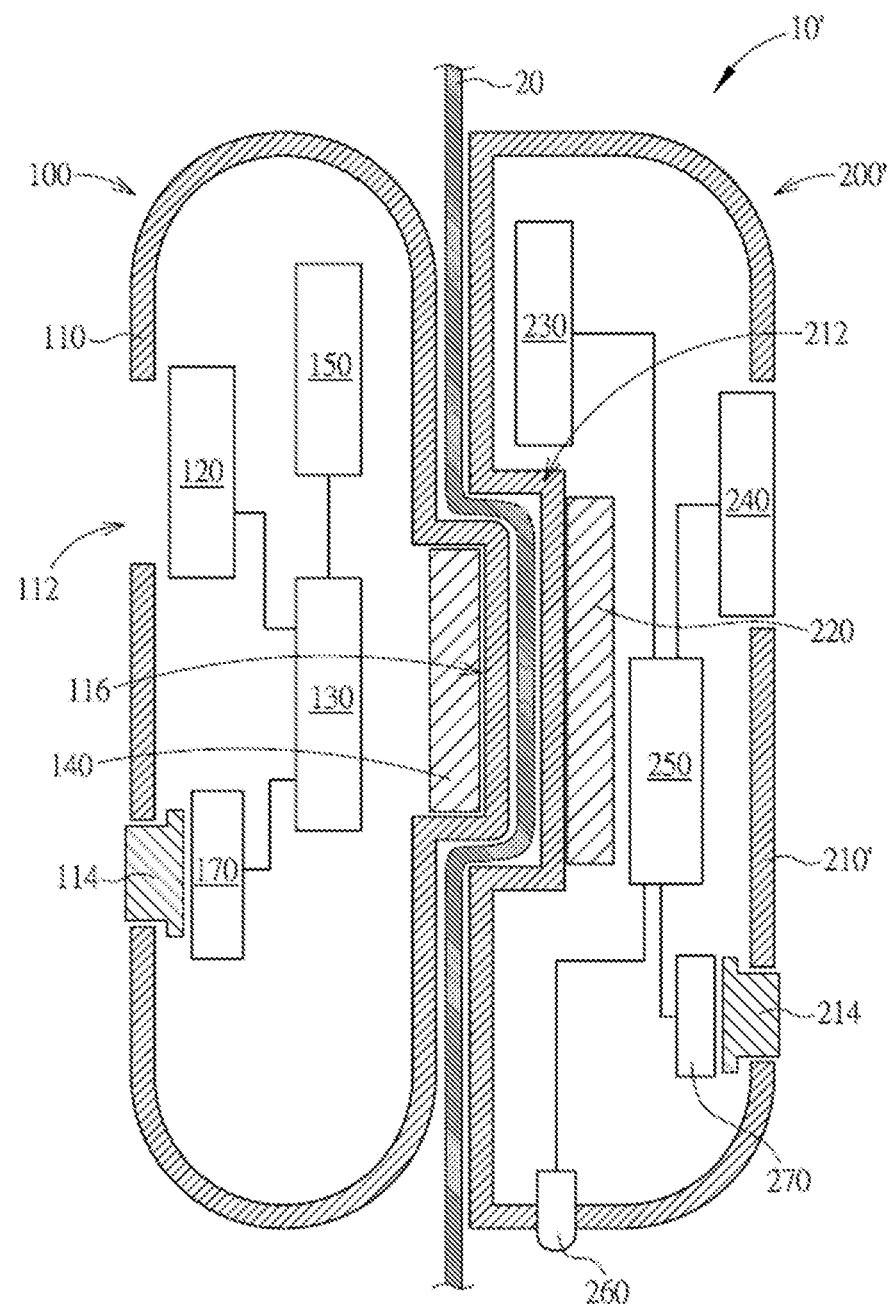
FIG. 2 is a diagram showing a second embodiment of the physiological status monitoring device of the present invention.

Please refer to FIG. 2. FIG. 2 is a diagram showing a second embodiment of the physiological status monitoring device of the present invention. As shown in FIG. 2, the monitoring module 100 of the physiological status monitoring device 10' of the present invention is similar to the monitoring module of FIG. 1. Therefore, no further illustration is provided. The fixing module 200' of the physiological status monitoring device 10' of the present invention can further comprise a second wireless transmission module 230, a display unit 240 and a second processing unit 250. The second wireless transmission module 230 is configured to receive the monitoring result transmitted from the first wireless transmission module 150. For example, the first wireless transmission module 150 can be an infrared transmission module and the second wireless transmission module 230 can be an infrared receiver module. The first wireless transmission module 150 can transmit the monitoring result to the second wireless transmission module 230 by infrared. In addition, each of the first housing 110 and the second housing 210 can be formed with an opening in order to facilitate infrared transmission and reception of the first wireless transmission module 150 and the second wireless transmission module 230. In the above embodiment, the first wireless transmission module 150 and the second wireless transmission module 230 are illustrated as examples. The first wireless transmission module 150 and the second wireless transmission module 230 of the present invention are not limited to the above embodiment. The second processing unit 250 is electrically connected to the second wireless transmission module 230 and the display unit 240. The second processing unit 250 is configured to control the display unit 240 to display the monitoring result.

In addition, the fixing module 200' can further comprise an indication light 260 for indicating the monitoring result of the monitoring unit 120. For example, when the second processing unit 250 determines that a body temperature of a monitored target is over a predetermined value, the second processing unit 250 can control the indication light 260 to emit warning light, in order to notify the medical personnel or related personnel that the body temperature of the monitored target is too high.

On the other hand, the fixing module 200' can further comprise a switch 270 for generating a control signal to the second processing unit 250. For example, the switch 270 can be a pushbutton switch. The second housing 210 can further has a pressing structure 214 corresponding to the switch 270. When the pressing structure 214 is pressed, the switch 270 is activated to generate a control signal to the second processing unit 250. The second processing unit 250 can control the display unit 240 to perform a corresponding operation (such as displaying the measured physiological status or notifying the monitoring unit 120 to measure the physiological status of the human body through the first wireless transmission module 150 and the second wireless transmission module 230) according to the control signal. Moreover, in the present invention, the switch 270 is not limited to the pushbutton switch. The switch 270 can be selected from other types of switches, such as a touch sensing switch. The user can activate the switch by touch. When the switch 270 is a touch sensing switch or other type of switch, the second housing 210 can have another corresponding structure.

In contrast to the prior art, the physiological status monitoring device of the present can be easily fixed to the flexible object by magnetic force, so as to continuously or periodically monitor the physiological status of the human body without being attached to skin. Therefore, the physiological status monitoring device of the present invention can prevent skin allergy or discomfort caused by attaching the physiological status monitoring device to the skin.

Those skilled in the art will readily observe that numerous modifications and alterations of the device and method may be made while retaining the teachings of the invention.

What is claimed is:

1. A physiological status monitoring device, comprising:
    a monitoring module, comprising:
    a first housing configured to be arranged at a first side of a flexible object;
    a sensor, arranged in the first housing, for monitoring a physiological status of a human body;
    a first processing unit, electrically connected to the sensor, for controlling operations of the sensor; and
    a first magnetic fixing unit connected to the first housing; and
    a fixing module, comprising:
    a second housing configured to be arranged at a second side of the flexible object; and
    a second magnetic fixing unit connected to the second housing;
    wherein the first magnetic fixing unit and the second magnetic fixing unit are configured to hold the first housing and the second housing on the flexible object by magnetic force,
    wherein one of the first housing and the second housing has a recessed structure, and the other one of the first housing and the second housing has a protrusion structure corresponding to the recessed structure, wherein a shape of the protrusion structure and a shape of the recessed structure are configured to be complement to each other,
    wherein one of the first magnetic fixing unit and the second magnetic fixing unit is disposed in the recessed structure, and the other one of the first magnetic fixing unit and the second magnetic fixing unit is disposed in the protrusion structure,
    wherein the protrusion structure and the recessed structure are attracted and engaged with each other by a magnetic force between the first magnetic fixing unit and the second magnetic fixing unit, and an entire surface of the protrusion structure and an entire surface of the recessed structure are separated by the flexible object, such that the flexible object is held and fixed by a clamping force between the protrusion structure and the recessed structure and the clamping force is enhanced by the magnetic force, and the physiological status monitoring device is fixed to the flexible object by the clamping force and the magnetic force without being attached to skin of the human body.

2. The physiological status monitoring device of claim 1, wherein the sensor is a non-contact type sensor.

3. The physiological status monitoring device of claim 2, wherein the sensor is configured to monitor at least one of body temperature, heart rate and respiration of the human body.

4. The physiological status monitoring device of claim 1, wherein the sensor is configured to monitor at least one of body temperature, heart rate and respiration of the human body.

5. The physiological status monitoring device of claim 1, further comprising an indication light configured in the second housing, wherein the indication light is indicating a monitoring result of the sensor arranged in the first housing.

6. The physiological status monitoring device of claim 1, wherein the monitoring module further comprises a wireless transmitter wirelessly transmitting a monitoring result of the sensor, wherein the wireless transmitter is configured in the first housing.

7. The physiological status monitoring device of claim 6, wherein the wireless transmitter is a Bluetooth transmitter wirelessly transmitting the monitoring result to an external electronic device.

8. The physiological status monitoring device of claim 6, wherein the fixing module further comprises:
    a wireless receiver configured in the second housing and to receive the monitoring result transmitted from the wireless transmitter;
    a display unit configured in the second housing; and
    a second processing unit, configured in the second housing and electrically connected to the wireless receiver and the display unit, controlling the display unit to display the monitoring result.

9. The physiological status monitoring device of claim 8, wherein the wireless transmitter is an infrared transmitter and the wireless receiver is an infrared receiver.

10. The physiological status monitoring device of claim 1, further comprising a switch configured to generate a control signal to the first processing unit.

* * * * *